United States Patent [19]

Weber

[11] 4,382,921

[45] May 10, 1983

[54] METHOD FOR TREATMENT OF PSORIASIS

[76] Inventor: Gerhard Weber, Virchowstrasse 5, 8500 Nürnberg, Fed. Rep. of Germany

[21] Appl. No.: 259,530

[22] Filed: May 1, 1981

[30] Foreign Application Priority Data

May 7, 1980 [DE] Fed. Rep. of Germany ....... 3017390
Apr. 11, 1981 [DE] Fed. Rep. of Germany ....... 3114824

[51] Int. Cl.³ ............................................. A61K 37/00
[52] U.S. Cl. .................................................... 424/177
[58] Field of Search ........................................ 424/177

[56] References Cited

FOREIGN PATENT DOCUMENTS 3114824 8/1982 Fed. Rep. of Germany ...... 424/177

OTHER PUBLICATIONS

Weber, et al., "Psoriasis and Human Growth Hormone: Aetiology and Therapy", 361–365 (1981).
Computer Printout (1980).

*Primary Examiner*—Delbert R. Phillips
*Attorney, Agent, or Firm*—Toren, McGeady and Stanger

[57] ABSTRACT

A method for the treatment of psoriasis comprising administering an anti-psoriasis effective amount of an antagonist of the growth hormone.

5 Claims, No Drawings

METHOD FOR TREATMENT OF PSORIASIS

BACKGROUND OF THE INVENTION

1. Field of the Invention

This invention relates to a method for the treatment of psoriasis.

2. Description of the Prior Art

Large segments of the population are affected by psoriasis. However, the cause of this disease is thus far unknown, see, for example, Brockhaus Encyclopedic Dictionary 1972, Vol. 15, Page 224. Generally, the treatments described in this reference include treatments with corticosteroids which can achieve a certain amount of a short term regression of the disease. This method as well as other methods known today have not produced a complete cure.

SUMMARY OF THE INVENTION

I have discovered a method for the treatment of psoriasis which has achieved significant regression of the disease. My invention is based on the discovery that the cause of psoriasis is a persistence of the secretion of the human growth hormone, i.e., somatotropic hormone). Thus, the invention comprises the administration of an antagonist for the growth hormone in amounts effective to sufficiently antagonize the secretion of the hormone to normalize the psoriasis.

DESCRIPTION OF THE PREFERRED EMBODIMENT

Several antagonists for the growth hormone or somatotropic hormone can be utilized in accordance with the present invention. For example, somatostatine which is a tetra-decapeptide can be used. The only indication for somatostatine thus far is hypophysical gigantism as well as the assisted storage of insulin in diabetes. Of course, neither of these indications bear any resemblance to psoriasis.

An example of the primary structure of somatostatine is:

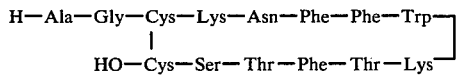

Another antagonist which can be used is bromocriptine. Like somatostatine, bromocriptine acts on the pituitary gland as a growth inhibitor. This indication, however, also bears no resemblance to psoriasis.

Finally, it is possible to use a combination of somatostatine and bromocriptine either together, or sequentially in the treatment of psoriasis. In any event, the amount of the dosage should be that amount which is effective to terminate the psoriasis. This amount may vary from patient to patient.

Typical dosages and applications of somatostatine are as follows:

| | |
|---|---|
| 1. | 250 μg/hr/48 hrs. (that is to say, 250 μg per hour and for 48 hours as continuous intravenous drip, e.g., in 5% glucose solution). This can be followed by: |
| 1.2.1 | 250 μg infusion 2 × daily, or |
| 1.2.2 | 1000 μg infusion in 24 hours, or |
| 1.3.1 | a subcutaneous injection of 250 μg 2 × in 24 hours, or |
| 1.3.2 | a subcutaneous injection of 1000 μg every 24 hours, or |
| 1.4.1 | a nasal spray of 500 μg every 24 hours, or |
| 1.4.2 | a nasal spray of 1000 μg every 24 hours, or |
| 1.5.1 | capsules with a total of 500 μg every 24 hours, or |
| 1.5.2 | capsules with a total of 1000 μg every 24 hours. |

The dosages and sequence numbered 1.2.1 to 1.5.2 are alternative. An interval of up to four days without treatment can be inserted between any one of these treatments and the 48 hour interval after step 1. However, it is also possible to utilize the sequential treatments 1.2.1 to 1.5.2 without the prior continuous intravenous drip specified in step 1.

As noted, the respective application and dosages may be adjusted depending on the disease in the specific patient as well as the condition, reaction sensitivity, etc. of the patient. The treatment should be continued until complete regression of the psoriasis has occurred. If a relapse does occur, renewed treatment with somatostatine has proven to be successful.

Treatment with bromocriptine has been effected in the following manner utilizing tablets with 2.5 mg of bromocriptine.

| | 6.00 A.M. | 12.00 Noon | 6.00 P.M. | 10.00 P.M. |
|---|---|---|---|---|
| 1st day | 1 | | | |
| 2nd day | 1 | | 1 | |
| 3rd day | 1 | 1 | 1 | |
| 4th day | 1 | 1 | 1 | 1 |
| 5th day | 2 | 1 | 1 | 1 |
| 6th day | 2 | 1 | 2 | 1 |
| 7th day | 2 | 2 | 2 | 1 |
| 8th day | 2 | 2 | 2 | 2 |

(the numbers refer to the number of tablets of 2.5 mg of bromocriptine)

On the 9th day, if there is tolerance, one capsule of 10 mg at 6.00 A.M. and 6.00 P.M. respectively are administered. The administration is oral and is continued until a complete cure is effected.

I claim:

1. A method for treating psoriasis comprising administering an effective amount of an antagonist of the somatotropic hormone.

2. The method of claim 1 wherein the antagonist is in the form of somatostatine.

3. The method of claim 1 wherein the antagonist is in the form of bromocriptine.

4. The method of claim 1 wherein as the antagonists, a combination of somatostatine and bromocriptine are used.

5. The method of claim 1 wherein somatostatine and bromocriptine are used consecutively as the antagonists.

* * * * *